(12) United States Patent
Kim et al.

(10) Patent No.: US 8,062,597 B2
(45) Date of Patent: Nov. 22, 2011

(54) DISCOLORATION INDICATORS FOR CHECKING LIFE SPAN OF DESULFURIZATION DISORBENT, AND DESULFURIZATION REACTOR AND DESULFURIZATION SYSTEM COMPRISING THE SAME

(75) Inventors: Myung Jun Kim, Daejeon (KR); Young Seek Yoon, Daejeon (KR); Jin Hong Kim, Daejeon (KR)

(73) Assignee: SK Energy Co., Ltd., Seoul (KR)

( * ) Notice: Subject to any disclaimer, the term of this patent is extended or adjusted under 35 U.S.C. 154(b) by 370 days.

(21) Appl. No.: 12/309,125

(22) PCT Filed: Jul. 11, 2007

(86) PCT No.: PCT/KR2007/003361
§ 371 (c)(1),
(2), (4) Date: Jan. 6, 2009

(87) PCT Pub. No.: WO2008/007899
PCT Pub. Date: Jan. 17, 2008

(65) Prior Publication Data
US 2009/0311144 A1     Dec. 17, 2009

(30) Foreign Application Priority Data
Jul. 11, 2006   (KR) .................. 10-2006-0064990

(51) Int. Cl.
*A61L 2/28* (2006.01)
*B01J 10/00* (2006.01)
*B01J 19/00* (2006.01)
*B01J 8/00* (2006.01)
*G01N 21/00* (2006.01)
*G01N 21/75* (2006.01)

(52) U.S. Cl. .......... 422/119; 422/129; 422/600; 436/80; 436/164

(58) Field of Classification Search .................. 422/119, 422/600, 129; 436/164, 80
See application file for complete search history.

(56) References Cited

U.S. PATENT DOCUMENTS
3,350,175 A * 10/1967 Clay et al. .................... 422/413
(Continued)

FOREIGN PATENT DOCUMENTS
JP          63223188 A  *  9/1988
(Continued)

OTHER PUBLICATIONS
Machine translation of JP 2002-358992A, which was published on Dec. 13, 2002.*
(Continued)

*Primary Examiner* — Walter Griffin
*Assistant Examiner* — Natasha Young
(74) *Attorney, Agent, or Firm* — Abelman, Frayne & Schwab

(57) ABSTRACT

This invention relates to a discoloration indicator for checking the life span of a desulfurization adsorbent, and a desulfurization reactor and a desulfurization system including the same, and specifically, to a discoloration indicator for checking the life span of a desulfurization adsorbent able to effectively adsorb and remove organic sulfur compounds from fossil fuels, including natural gas or LPG containing the organic sulfur compound, and to a desulfurization reactor and a desulfurization system including the same. This invention makes it possible to remove the organic sulfur compound using the desulfurization adsorbent and to check the replacement time of the adsorbent with the naked eye or using an electrical signal, and thus may be applied to the treatment of natural gas or LPG requiring desulfurization, and also to hydrogen generators for home fuel cell generation systems or distributed fuel cell generation systems requiring that devices be simple, or requiring unmanned operation.

13 Claims, 2 Drawing Sheets

U.S. PATENT DOCUMENTS

| | | | | | |
|---|---|---|---|---|---|
| 4,277,368 | A | * | 7/1981 | Amy et al. | 436/174 |
| 5,120,511 | A | * | 6/1992 | Luft | 422/86 |
| 5,833,882 | A | * | 11/1998 | Shimada et al. | 252/408.1 |
| 6,042,798 | A | | 3/2000 | Masuda et al. | |
| 2005/0214199 | A1 | * | 9/2005 | Hayashi et al. | 423/599 |
| 2008/0090115 | A1 | * | 4/2008 | Saito et al. | 429/19 |

FOREIGN PATENT DOCUMENTS

| | | | |
|---|---|---|---|
| JP | 2002316043 A | * | 10/2002 |
| JP | 2002358992 | | 12/2002 |
| JP | 2003/020489 | | 1/2003 |
| JP | 2004/099826 | | 4/2004 |
| KR | 1020050003351 A | | 1/2005 |
| WO | WO 2006/068135 A1 | * | 6/2006 |

OTHER PUBLICATIONS

Machine translation of JP 2002-316043A, which was published on Oct. 29, 2002.*

First Notification of Office Action from The State Intellectual Property Office of P.R. China dated May 21, 2010 of Application No. 200780025078.7.

McCarty et al.; Thermodynamics of sulfur chemisorption on metals I. alumina-supported nickel; *J.Chem.Phys.* 72:12 (1980) 6332-6337.

McCarty et al.; Thermodynamics of sulfur chemisorption on metals II. alumina-supported ruthenium[a)]; *J.Chem.Phys.* 74:10 (1981) 5877-5880.

Satokawa et al. Adsorptive removal of dimethylsulfide and *t*-butylmercaptan from pipeline natural gas fuel on Ag zeolites under ambient conditions; *J.Apcathb.* 56 (2005) 51-56.

M.V. Twygg; Catalyst Handbook; *Oxford University Press*, 2 Ed.(1997) 278-279.

* cited by examiner

DISCOLORATION INDICATORS FOR CHECKING LIFE SPAN OF DESULFURIZATION DISORBENT, AND DESULFURIZATION REACTOR AND DESULFURIZATION SYSTEM COMPRISING THE SAME

TECHNICAL FIELD

The present invention relates to a discoloration indicator for checking the life span of a desulfurization adsorbent, and a desulfurization reactor including the same, and, more particularly, to a discoloration indicator, which enables checking of the replacement time of an adsorbent for removing an organic sulfur compound from natural gas, and to a desulfurization reactor and a desulfurization system including the same.

BACKGROUND ART

Conventionally, in natural gas mainly used as fuel, a small amount of an organic sulfur compound, such as t-butylmercaptan (TBM), tetrahydrothiophene (THT), and dimethylsulfide (DMS), is included as an odorant in order to make known the danger occurring upon leakage thereof. At present, natural gas, which is domestically supplied, is known to contain THT and TBM organic sulfur compounds mixed at a ratio of about 7:3, in which the total concentration of the odorant is about 4 ppm (15 mg/m$^3$) (Korean Unexamined Patent Publication No. 2005-003351). Further, the odorant is contained in liquefied petroleum gas (LPG), the main component thereof includes DMS (dimethylsulfide) and TBM, and the total amount of the odorant is limited to about 30 ppm.

Although the organic sulfur compound odorant is required in the interest of preventing gas leakage accidents from becoming severe, in the case where natural gas or LPG is used as feed stock for hydrogen or synthesis gas, a poisoning phenomenon, which gradually decreases the activity of the catalyst during steam reforming, is caused. In the case of a typical steam reforming catalyst, the concentration of sulfur (S) allowable at an operation temperature of 700° C. is approximately 0.1 ppm (Catalysts Handbook 2$^{nd}$ Ed.). In practice, steam reforming for producing a reformed gas containing concentrated hydrogen through reaction between natural gas or LPG and steam is conducted using, as a reforming catalyst, a transition metal catalyst or a precious metal catalyst. As such, there are reports that these catalysts are easily poisoned by sulfur and sulfur compounds are formed on the catalyst surface thereof at concentrations as low as ppm or less (McCarty et al; J. Chem. Phys. Vol. 72, No. 12, 6332, 1980, J. Chem. Phys. Vol. 74, No. 10, 5877, 1981).

Thus, in the case where the fuel is used to prepare hydrogen or synthesis gas through steam reforming, the steam reforming catalyst is poisoned by sulfur, undesirably decreasing the activity of the catalyst. Accordingly, there is a need to perform desulfurization using a desulfurizing agent during steam reforming. Typical methods of removing the organic sulfur compound from hydrocarbon fuel include hydrodesulfurization. Hydrodesulfurization includes adding hydrogen to hydrocarbon fuel, decomposing an organic sulfur compound into hydrogen sulfide using a cobalt-molybdenum catalyst or nickel-molybdenum catalyst supported on alumina, and absorbing the produced hydrogen sulfide on a desulfurizing agent such as zinc oxide or iron oxide to thus remove it, as seen in Reactions 1 and 2 below.

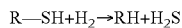  Reaction 1

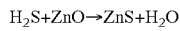  Reaction 2

Through hydrodesulfurization and the subsequent absorption of hydrogen sulfide, the sulfur component contained in natural gas or LPG is known to decrease to about 0.1 ppm. However, because hydrodesulfurization and subsequent absorption are conducted at high temperatures of about 300~450° C., a long period of time is taken to increase the temperature of the catalyst or absorbent, and furthermore, upon application to steam reforming, because some of the hydrogen prepared using a steam reformer is refluxed and then fed into a desulfurization reactor, the procedure thereof is complicated. Such operational problems may adversely affect hydrogen generators for residential fuel cell power generation systems or distributed fuel cell power generation systems, which require that devices be simple or that starting be rapid.

With the goal of removing sulfur from natural gas or LPG at lower temperatures without the use of hydrogen, by Osaka Gas, Japan, a copper-zinc desulfurization absorbent was developed through co-precipitation to thus apply it to the removal of thiophene at high temperatures (U.S. Pat. No. 6,042,798). However, this is disadvantageous because the temperature of the absorbent should be maintained at 200° C. or higher to assure a predetermined level or more of desulfurization efficiency.

TBM, THT, and DMS, which are odorants contained in natural gas or LPG, are known to be adsorbed on activated carbon or zeolite material at room temperature. Tokyo Gas, Japan, using an activated carbon fiber adsorbent having excellent adsorption desulfurization capability and an adsorbent resulting from ion-exchange of hydrophilic zeolite with one or two transition metals selected from among Ag, Fe, Cu, Ni, and Zn, removed a dimethyl sulfide (DMS) odorant from fuel gas (Japanese Unexamined Patent Publication Nos. 2003-20489 and 2004-99826). These desulfurization adsorbents are advantageous because different adsorbents having the ability to adsorb the sulfur compound are provided at the upper portion and the lower portion of a desulfurization reactor, or a mixture of two or more different adsorbents having the ability to adsorb the sulfur compound is provided, and thus it is possible to use them either at room temperature or at low temperatures. As one type among the desulfurization adsorbents, useful is an adsorbent in which a transition metal such as silver is supported on zeolite through ion exchange. Although an adsorbent, prepared by ion-exchanging or impregnating Na—Y zeolite with silver, exhibited DMS adsorption performance superior to activated carbon adsorbents when it contained 5 wt % or more of silver based on the total amount of the adsorbent, the TBM (t-butylmercaptan) adsorption performance thereof was similar to that of activated carbon only when the content of silver was increased to 18 wt % (Satokawa et al., Applied Catalysis B: Environmental, 56 (2005), p 51-56).

The desulfurization adsorbent may be regenerated by flowing steam, and adsorption and regeneration are repeated using two or more adsorption towers mounted in large-scale plants. However, in the case where miniaturization and lightweight are regarded as important, as in a residential fuel cell power generation system or a distributed fuel cell power generation system, it is difficult to provide a plurality of adsorption reactors to continuously conduct adsorption and regeneration. Thus, when comparing the activated carbon adsorbent with the silver-containing zeolite adsorbent from the point of views mentioned above, the activated carbon adsorbent has superior performance relative to the price thereof. However, in the case where only the activated carbon adsorbent is used, there is a problem in which the concentration of sulfur in gas flow discharged from the gas outlet of the adsorption reactor must be periodically analyzed using a predetermined gas analyzer in order to check the life span of the adsorbent. Further, the adsorption reactor should be replaced within a predetermined period usually before fully utilizing the adsorption capacity of the adsorbent. However, these problems may become more serious upon individual installation at independent places, like residential fuel cell power generation systems or distributed fuel cell power generation systems, unlike large-scale plants.

DISCLOSURE

Technical Problem

Accordingly, the present inventors have noticed that a silver and/or manganese compound is discolored when it reacts with a sulfur compound, and thus, in order to easily check the replacement time of a desulfurization adsorbent for effectively adsorbing and removing an organic sulfur compound from fossil fuels, such as natural gas or LPG, containing an organic sulfur compound, a discoloration indicator, in which a silver and/or manganese compound is supported or applied on alumina, silica, zeolite, or silica gel, is provided, thereby making it easier to check the replacement time of the desulfurization adsorbent, so that desulfurization may be more economically and simply conducted, consequently completing the present invention.

Therefore, the present invention provides a discoloration indicator for easily checking the replacement time of a desulfurization adsorbent upon desulfurization.

In addition, the present invention provides a desulfurization reactor, which may be easily applied to processes requiring desulfurization and facilitates the estimation of the replacement time of the adsorbent.

In addition, the present invention provides a desulfurization system, which facilitates the estimation of the replacement time of the adsorbent and is useful for desulfurization.

Technical Solution

According to the present invention, a discoloration indicator for checking the replacement time of a desulfurization adsorbent may include a support, such as alumina, silica, zeolite, or silica gel, and a silver compound, a manganese compound, or a mixture thereof, which is supported or applied thereon.

In addition, according to the present invention, a desulfurization reactor may include a closed container having a gas inlet and a gas outlet formed at respective ends thereof; and a desulfurization adsorbent and the discoloration indicator according to the invention sequentially loaded from the direction of introduction of gas in the closed container.

In addition, according to the present invention, a desulfurization system may include the desulfurization reactor according to the invention; a discoloration sensor, for example, optical photo sensor, connected to the desulfurization reactor to sense the discoloration of the discoloration indicator; a signal amplifier for amplifying the signal of the discoloration sensor; and a controlling/monitoring system for remotely controlling or monitoring desulfurization.

Advantageous Effects

According to the present invention, the discoloration indicator functions to easily check the replacement time of a desulfurization adsorbent. The desulfurization reactor may be simply applied to all application fields requiring the removal of an organic sulfur compound from natural gas or LPG, and in particular, may be usefully applied to hydrogen generators for residential fuel cell power generation systems or distributed fuel cell power generation systems requiring that devices be simple or that stand-alone operation be realized.

Figure 1:
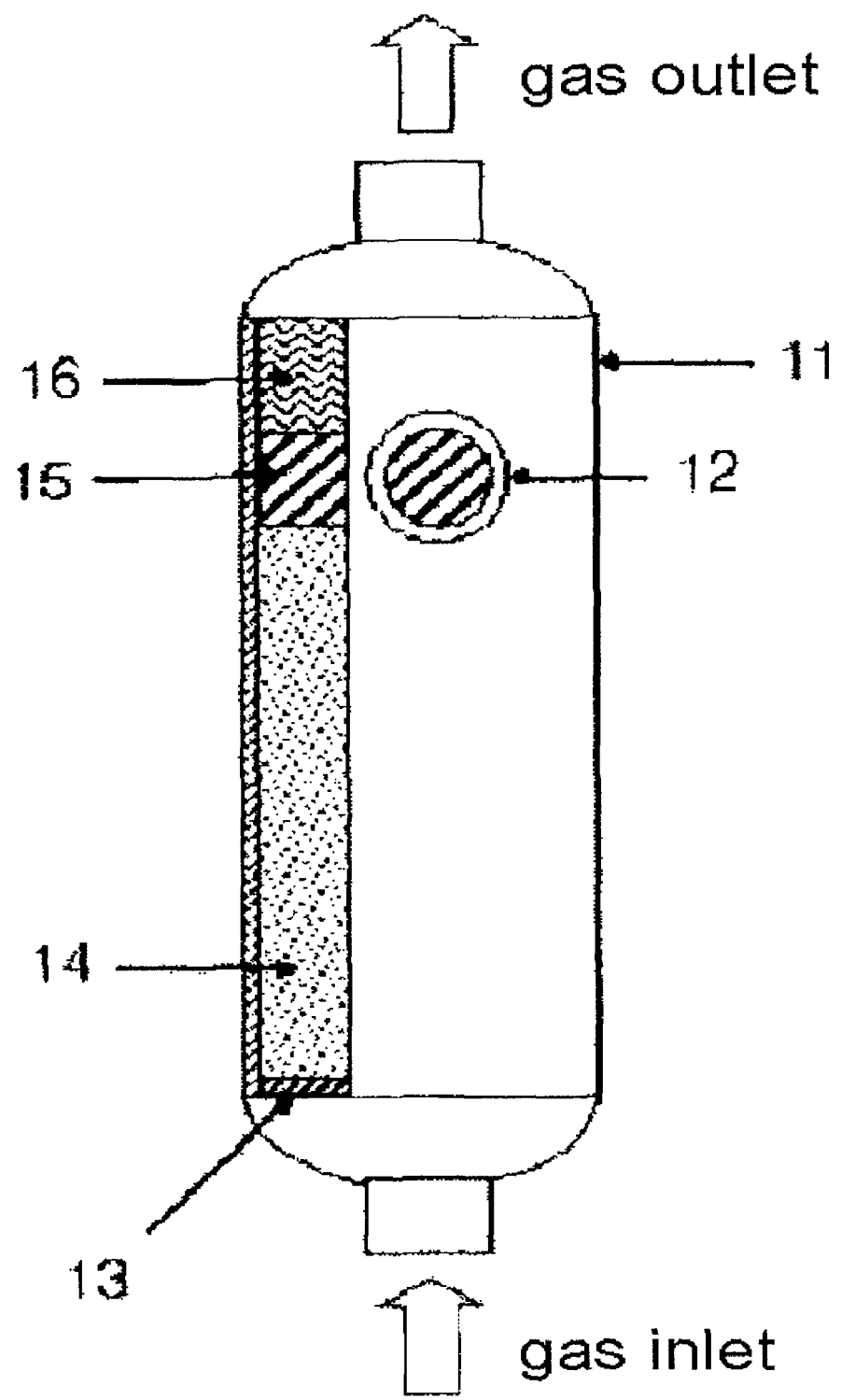
FIG. 1 schematically illustrates the shape of the adsorption reactor, which includes the discoloration indicator according to the present invention, the adsorbent, and the discoloration indicator.

DESCRIPTION OF THE REFERENCE NUMERALS IN THE DRAWINGS 11 and 21: adsorption desulfurization reactor
12: sight window
13: adsorbent-supporting plate
14: adsorbent A
15: discoloration indicator
16: adsorbent B
22: discoloration sensor
23: signal amplifier
24: PLC
25: controlling or monitoring system

BEST MODE

Hereinafter, a detailed description will be given of the present invention.

As mentioned above, the present invention pertains to a discoloration indicator for checking the replacement time of a desulfurization adsorbent, which may be easily applied to the treatment of natural gas or LPG requiring desulfurization by enabling checking of the replacement time of the desulfurization adsorbent upon the removal of an organic sulfur compound using the desulfurization adsorbent, and to a desulfurization reactor and a desulfurization system including the same.

The discoloration indicator of the present invention is provided in a form in which a silver compound, a manganese compound, or a mixture thereof is supported or applied on a support, such as alumina, silica, zeolite, or silica gel. According to the embodiment of the present invention, silver nitrate ($AgNO_3$) or manganese nitrate ($Mn(NO_3)_2$) may be supported on silica gel, commonly used as the adsorbent, thereby simply and inexpensively preparing a discoloration indicator.

According to the present invention, the amount of the silver compound, the manganese compound, or the mixture thereof, which is supported or applied on the support, is preferably set to 0.1~10 wt % and more preferably 0.5~5 wt % based on the amount of the support. When the amount is less than 0.1 wt % the ability to judge the degree of discoloration due to contact with organic sulfur is deteriorated. On the other hand, when the amount exceeds 10 wt %, it is difficult to uniformly support the silver or manganese compound, and there are no significant improvement effects for discoloration properties despite an increase in sulfur adsorption performance.

Because the discoloration indicator of the present invention is discolored through a chemical reaction upon the adsorption of the sulfur compound, it is possible to check the replacement time of the desulfurization adsorbent.

In the present invention, the desulfurization reactor and the desulfurization system, including the discoloration indicator, are provided. According to the embodiment of the present invention, the desulfurization reactor includes a gas inlet for introducing gas and a gas outlet for discharging gas at respective ends thereof, and (i) a desulfurization adsorbent using activated carbon or zeolite as a main medium and (ii) a discoloration indicator composed mainly of silver or manganese are sequentially loaded therein along the direction from the introduction to the discharge of gas. Further, a sight window for observing the discoloration of the discoloration indicator may be provided. The desulfurization system using the desulfurization reactor of the present invention may include a discoloration sensor, for sensing the discoloration of the discoloration indicator in the desulfurization reactor to thus generate an electrical signal, and a signal amplifier, but the present invention is not limited thereto.

Below, the present invention is described in detail with reference to the appended drawings.

Figure 2:
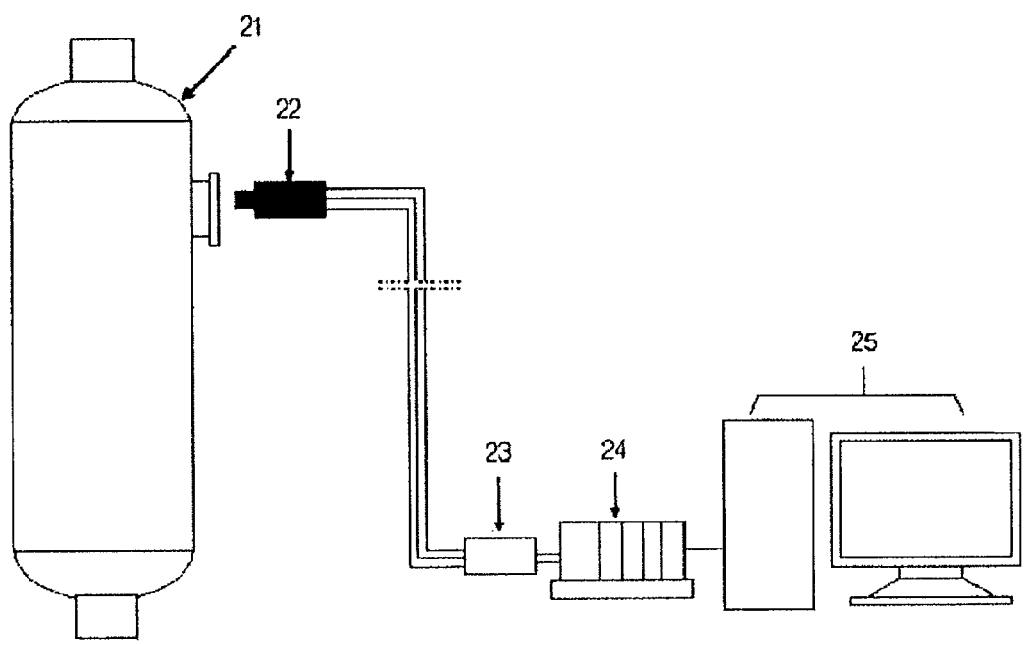
FIG. 2 illustrates the monitoring system including the desulfurization reactor, in which the state of discoloration of the discoloration indicator according to the present invention is converted into an electrical signal, thus enabling checking of the life span of the adsorbent.

FIG. 1 illustrates the desulfurization reactor 11 according to the present invention, including desulfurization adsorbents 14 and 16, a discoloration indicator 15, and a sight window 12, and FIG. 2 schematically illustrates the desulfurization system according to the present invention, including a desulfurization reactor 21, a discoloration sensor 22, a signal amplifier 23, a PLC 24 for control or signal conversion, and a controlling/monitoring system 25 for remotely controlling or monitoring the entire process, including the desulfurization reactor.

As illustrated in FIG. 1, natural gas or LPG containing an organic sulfur compound is introduced into the lower end of the desulfurization reactor 11, is passed through the first desulfurization adsorbent (or desulfurization adsorbent A) 14, the discoloration indicator 15, and the second desulfurization adsorbent (or desulfurization adsorbent B) 16, and is then discharged in a sulfur-free state. The degree of removal of sulfur may vary depending on gas hourly space velocity (GHSV, $hr^{-1}$), linear velocity in the adsorption reactor, or the temperature of gas introduced, and sulfur may be typically reduced to the level of ones of ppb or less.

The desulfurization adsorbent A 14 is activated carbon itself, impregnated activated carbon, in which an alkali metal salt or a transition metal is supported or applied on activated carbon, or zeolite. When the desulfurization adsorbent A is loaded into the desulfurization adsorption reactor, it is provided in the lower portion of the adsorption reactor, into which natural gas or LPG is introduced. The adsorbent A, which is used to remove most of the sulfur, may be loaded in an amount of 70~80 vol % based on the volume of the desulfurization reactor. When the above adsorbent is loaded in an amount less than 70 vol %, the replacement period of the desulfurization reactor is decreased. On the other hand, when the above adsorbent is loaded in an amount greater than 80 vol %, the space where the discoloration indicator is loaded becomes too small, undesirably making it difficult to sufficiently exhibit desired effects. To check the termination of the life span of the adsorbent A, a predetermined amount of the discoloration indicator of the present invention is loaded on the desulfurization adsorbent A.

In the preset invention, the amount of loaded discoloration indicator is not particularly limited, and may be determined so that it is enough to check the discoloration depending on the shape of the adsorption reactor or the size of the sight window. The amount thereof is set to 20~30 vol % based on the volume of the desulfurization reactor. If the indicator is loaded in an amount less than 20 vol %, it is difficult to realize sufficient indicating effects in the case where gas flow becomes non-uniform due to the phenomenon of channeling in the reactor. On the other hand, if the indicator is loaded in an amount more than 30 vol %, the amount of loaded adsorbent A is greatly decreased, undesirably decreasing the replacement period of the desulfurization reactor.

In the case where the conditions of introduction of natural gas or LPG into the desulfurization reactor drastically fluctuate, for example, in the case where an excess of natural gas or LPG is introduced into the desulfurization reactor or in the case where the formation of normal gas paths, such as channeling, is not realized in the adsorbent layer, there may occur a problem of slippage of organic sulfur even when the discoloration of the discoloration indicator progresses. This problem may be overcome by further loading the desulfurization adsorbent B on the discoloration indicator. As such, the desulfurization adsorbent A, the discoloration indicator, and the desulfurization adsorbent B may be loaded at a ratio of 70 to 80 vol %:10 to 20 vol %:10 to 20 vol %. In general, the desulfurization adsorbent B is the same as the desulfurization adsorbent A. However, in the case where $NO_2$ created as a by-product during discoloration as represented by Reaction 3 below must be removed, the use of a special adsorbent is required. That is, an adsorbent able to simultaneously adsorb organic sulfur and $NO_2$ is used. For example, activated carbon impregnated with alkali metal hydroxide may be used therefor.

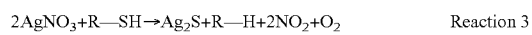

$$2AgNO_3 + R—SH \rightarrow Ag_2S + R—H + 2NO_2 + O_2 \qquad \text{Reaction 3}$$

The sight window 12, the shape of which is not limited, is manufactured in a form able to easily observe the state of the discoloration indicator, and is then attached to the desulfurization reactor. The material for the desulfurization reactor is not particularly limited, but includes metal, glass, and plastics. In the case where the desulfurization reactor is manufactured using glass or transparent plastic, there is no need to additionally provide a sight window.

The replacement of the desulfurization adsorbent may be judged by sensing the discoloration of the discoloration indicator with the naked eye or using a predetermined sensor. In a field where the entire system should be automatic for stand-alone operation, for example, in a residential fuel cell power generation system or a distributed fuel cell power generation system, a sensor may be used. The sensor for checking the discoloration typically includes an optical fiber sensor. The desulfurization reactor is mounted, and the initial color of the discoloration indicator is stored in the sensor. Thereafter, when the color of the indicator deviates from the initial color, this state is sensed by the sensor, which outputs an electrical signal.

Because the electrical signal typically output from the optical fiber sensor is very weak, a signal amplifier 23 is additionally provided, as illustrated in FIG. 2. The electrical signal amplified using the signal amplifier 23 is transmitted to the PLC (Programmable Logical Controller) 24 or the controlling or monitoring part, such as a microprocessor, for controlling or monitoring the operation of the entire system including the desulfurization reactor, for example, a home fuel cell generation system or a distributed fuel cell generation system.

According to the present invention, the adsorbents, such as activated carbon, which is inexpensive, typical, and widely known, impregnated activated carbon, in which a transition metal or alkali metal is supported or applied on activated carbon, or zeolite, along with the discoloration indicator of the invention are appropriately disposed and provided in the adsorption reactor, which enables the estimation of the replacement period of the adsorbent with the naked eye or the sensor through the sight window attached to the adsorption reactor. Thereby, the adsorption reactor may be easily applied to processes requiring desulfurization, makes it easy to check the replacement time of the adsorbent, and realizes both economic benefits and convenience, and furthermore, is expected to usefully serve for hydrogen generators for home fuel cell generation systems or distributed fuel cell generation systems, which require that devices be simple or require unmanned operation.

MODE FOR INVENTION

Below, a better understanding of the present invention may be obtained through the following examples, which are set forth to illustrate, but are not to be construed as the limit of the present invention.

EXAMPLE 1

0.66 g of manganese nitrate was completely dissolved in 50 cc of deionized water, thus preparing a supporting solution. The prepared solution was supported on spherical silica gel having a 4~6 mesh size. The supporting process was conducted using vacuum evaporation. While water was slowly evaporated, manganese nitrate was uniformly supported on the silica gel. Excess water was removed from the catalyst supporting solution at 65~70° C. for 1 hour. The prepared discoloration indicator was dried at 110° C. for 1 hour, thus removing additional water from the interior of the pores. Consequently, the discoloration indicator containing 1 wt % of manganese was prepared.

EXAMPLE 2

0.32 g of silver nitrate was completely dissolved in 50 cc of deionized water, thus preparing a supporting solution. The prepared solution was supported on spherical silica gel having a 4~6 mesh size. Then, subsequent preparation procedures were conducted in the same manner as in Example 1, thus preparing the discoloration indicator containing 1 wt % of silver.

In order to judge whether the prepared discoloration indicator was discolored due to contact with organic sulfur, 2 cc of the manganese-based discoloration indicator, in which manganese was supported, was loaded into a pyrex tube having an inner diameter of 10 mm. Thereafter, while a mixture gas of TBM and THT, having a concentration of 1 ppm, was allowed to flow at a flow rate of 30 cc per min, the color change before or after discoloration was observed. The same experiment was conducted for the silver-supported discoloration indicator. The results are given in Table 1.

TABLE 1

| Color Change of Discoloration Indicator by Organic Sulfur Compound | | |
|---|---|---|
| | Before Discoloration | After Discoloration |
| Mn-based Discoloration Indicator | Colorless Transparent | Blackish Brown |
| Ag-containing Discoloration Indicator | Colorless Transparent | Yellow |

According to the present invention, the discoloration indicator alone could adsorb the organic sulfur compound, and thus, during discoloration, sulfur was not detected downstream of the discoloration indicator layer. In the case of the silver-supported discoloration indicator, it discolored to transparent yellow upon contact with gas containing organic sulfur in an amount as low as 1 ppm. However, regardless of whether the concentration of sulfur was as high as 5 ppm or as low as 1 ppm, the above indicator was discolored to blackish brown upon contact for a long period of time. This was because silver nitrate was converted into silver sulfide ($Ag_2S$) through reaction with sulfur. Some of the silver nitrate has been converted into silver oxide (Reaction 3).

Even when manganese or silver is supported or applied on a porous support other than silica gel, for example, alumina, silica, zeolite, or silica gel, it is discolored upon contact with sulfur. Depending on the properties of the porous support, for example, surface area, pore volume, and chemical properties of the surface thereof, the amount supported or applied optimally thereon may vary, and furthermore, the color before or after discoloration may be changed.

EXAMPLE 3

An activated carbon adsorbent A (adsorption performance: 0.63 mol/L) having a 30~50 mesh size and the manganese-based discoloration indicator of Example 1 were loaded into a pyrex tube having an inner diameter of 10 mm at a volume ratio of 7:3. As such, the total loading height was 5 cm. Into the reactor filled with the adsorbent and the discoloration indicator, a mixture gas in which THT and TBM were mixed at a molar ratio of about 7:3 and the total concentration of a sulfur compound in methane was adjusted to 10 ppm was allowed to flow at a flow rate of 100 cc per min. The optical fiber sensor was mounted to the middle portion of the discoloration indicator, that is, ½ of the total height from the lower surface of the discoloration indicator. After 650 hours of flow of the mixture gas, the lower portion of the discoloration indicator began to be discolored. After an additional period of about 50 hours, the discoloration indicator was discolored to blackish brown to ½ of the total height thereof. At such, the signal generated from the discoloration sensor (optical fiber sensor) was appropriately processed through the PLC to thus generate a waning sound through a buzzer connected to the PLC at the same time that the adsorbent replacement signal was generated on the screen of the PC.

The invention claimed is:

1. A discoloration indicator for checking a replacement period of a desulfurization adsorbent, comprising a silica gel as a support, and a manganese compound, which is supported or applied on the support, and the manganese compound is supported or applied in an amount of 0.1 to 10 wt % based on an amount of the support.

2. A desulfurization reactor, comprising:
   a closed container having a gas inlet and a gas outlet formed at respective ends thereof; and
   a desulfurization adsorbent and the discoloration indicator of claim 1, sequentially loaded from a direction of introduction of gas in the closed container.

3. The desulfurization reactor according to claim 2, wherein a loading ratio of the desulfurization adsorbent to the discoloration indicator is 70~80:20~30.

4. A desulfurization system, comprising:
   the desulfurization reactor of claim 3;
   a discoloration sensor connected to the desulfurization reactor to sense discoloration of the discoloration indicator;

a signal amplifier for amplifying a signal of the discoloration sensor; and a controlling/monitoring system for remotely controlling or monitoring desulfurization.

5. The desulfurization system according to claim 4, wherein the desulfurization system is included in an operation system of a home fuel cell generation system or a distributed fuel cell generation system.

6. The desulfurization reactor according to claim 2, further comprising a desulfurization adsorbent loaded on the discoloration indicator, a loading ratio of the discoloration indicator A to the discoloration indicator B being 7~80:10~20:10~20.

7. A desulfurization system, comprising:

the desulfurization reactor of claim 6;

a discoloration sensor connected to the desulfurization reactor to sense discoloration of the discoloration indicator;

a signal amplifier for amplifying a signal of the discoloration sensor; and a controlling/monitoring system for remotely controlling or monitoring desulfurization.

8. The desulfurization system according to claim 7, wherein the desulfurization system is included in an operation system of a home fuel cell generation system or a distributed fuel cell generation system.

9. The desulfurization reactor according to claim 2, wherein the desulfurization adsorbent is one selected from among activated carbon, impregnated activated carbon, or a mixture thereof.

10. A desulfurization system, comprising:

the desulfurization reactor of claim 9;

a discoloration sensor connected to the desulfurization reactor to sense discoloration of the discoloration indicator;

a signal amplifier for amplifying a signal of the discoloration sensor; and a controlling/monitoring system for remotely controlling or monitoring desulfurization.

11. The desulfurization system according to claim 10, wherein the desulfurization system is included in an operation system of a home fuel cell generation system or a distributed fuel cell generation system.

12. A desulfurization system, comprising:

the desulfurization reactor of claim 2;

a discoloration sensor connected to the desulfurization reactor to sense discoloration of the discoloration indicator;

a signal amplifier for amplifying a signal of the discoloration sensor; and a controlling/monitoring system for remotely controlling or monitoring desulfurization.

13. The desulfurization system according to claim 12, wherein the desulfurization system is included in an operation system of a home fuel cell generation system or a distributed fuel cell generation system.

* * * * *

UNITED STATES PATENT AND TRADEMARK OFFICE
CERTIFICATE OF CORRECTION

| | | |
|---|---|---|
| PATENT NO. | : 8,062,597 B2 | Page 1 of 1 |
| APPLICATION NO. | : 12/309125 | |
| DATED | : November 22, 2011 | |
| INVENTOR(S) | : Kim et al. | |

It is certified that error appears in the above-identified patent and that said Letters Patent is hereby corrected as shown below:

Title page, Item (73) should read

(73) Assignee: SK Innovation Co., Ltd.

Signed and Sealed this
Twenty-sixth Day of June, 2012

David J. Kappos
*Director of the United States Patent and Trademark Office*